United States Patent [19]

Osawa et al.

[11] Patent Number: 5,126,434
[45] Date of Patent: Jun. 30, 1992

[54] MONOCLONAL ANTIBODY SPECIFIC FOR A HUMAN MACROPHAGE CHEMOTACTIC FACTOR

[75] Inventors: Toshiaki Osawa, Tokyo; Tadashi Hase; Naonobu Yoshizuka, both of Tochigi, all of Japan

[73] Assignee: Kao Corporation, Tokyo, Japan

[21] Appl. No.: 561,762

[22] Filed: Aug. 2, 1990

[30] Foreign Application Priority Data

Aug. 14, 1989 [JP] Japan .................. 1-207947

[51] Int. Cl.⁵ .......................... C07K 15/28; C12N 5/12
[52] U.S. Cl. .................... 530/387.9; 435/240.27; 435/70.21; 530/388.23
[58] Field of Search ............. 530/387; 435/240.27, 435/70.21

[56] References Cited

FOREIGN PATENT DOCUMENTS 2138297 5/1990 Japan .

OTHER PUBLICATIONS

Lerner Nature 299:592 1982.
Maurer et al, Methods in Enzymology 70:49 1980.
Altman et al. J. Immunology 115:18, 1975.
Patent Abstracts of Japan, vol. 10, No. 28 (C-326); & JP-A-60 181 018 (Kao Sekken K.K.).
Cellular Immunology, vol. 123, 1989, pp. 212–225, Academic Press, Inc.; N. Yoshizuka et al.: "Microphage chemotactic factor (MCF) produced by a human T cell hybridoma clone".

*Primary Examiner*—John Doll
*Assistant Examiner*—Paula Hutzell
*Attorney, Agent, or Firm*—Browdy and Neimark

[57] ABSTRACT

The present invention relates to a monoclonal antibody which specifically binds to a peptide having amino acid sequence (I) described below or having in part at least continuous 4 amino acid sequences of the amino acid sequence (I), and also to a process for producing a monoclonal antibody capable of specifically binding to the peptide represented by the following amino acid sequence:

H-Y-Leu-Gly-Arg-X-Asp-Gly-Ser-Glu-OH     (I)

wherein X represents Glu or Gln and Y represents Trp or Arg.

1 Claim, No Drawings

MONOCLONAL ANTIBODY SPECIFIC FOR A HUMAN MACROPHAGE CHEMOTACTIC FACTOR

BACKGROUND OF THE INVENTION

1. Field of the Invention

The present invention relates to a monoclonal antibody and more particularly, to a novel monoclonal antibody capable of specifically binding to a peptide having macrophage chemotactic activity and as well as to a process for production thereof.

The monoclonal antibody in accordance with the present invention has a property of being capable of specifically reacting with a lymphokine or cytokine having macrophage chemotactic activity. Thus, the monoclonal antibody may be effectively utilized, particularly for the clarification of various immune mechanisms or tissue staining, or in the medical field such in diagnosis, etc.

2. Statement of Prior Art

In general, macrophage chemotactic factor (hereafter simply referred to as MCF) is generally known to be a lymphokine having macrophage chemotactic activity which is specifically or non-specifically secreted from lymphocytes and lymphocytically established cells. It is already known that a high macrophage chemotactic activity is noted in the supernatant obtained by stimulating peripheral blood lymphocytes (hereafter simply referred to as PBL) with lectin, e.g., phytohemagglutinin (hereafter simply referred to as PHA), and then culturing the stimulated lymphocytes.

The macrophage chemotactic activity is recognized also in the culture supernatant of a hybridoma obtained by fusing a leukemia cell line and the stimulated lymphocyte described above in order to impart a persistently surviving property (Japanese Patent Application Laid-Open No. 60-181018).

On the other hand, it is considered in delayed-type hypersensitivity that MCF would take part in development of delayed-type hypersensitivity, since infiltration of macrophage, in addition to lymphocytes, in the tissue is remarkable about 48 hours after the time when the skin reaction reaches the maximum in a sensitized animal to which hypersensitivity reaction has been induced.

As stated above, MCF is defined by its activity of collecting macrophage to the reacted local area; its application to medical drugs as an antitumor agent is expected.

Structural analysis of MCF has already been made. Purification of MCF from the hybridoma obtained from peripheral blood lymphocyte and determination of its primary structure were made by the present inventors (Japanese Patent Application No. 63-173785). Furthermore, MCF was also synthesized by chemical synthesis. The primary structure of MCF is shown by the following formula (I):

H-Y-Leu-Gly-Arg-X-Asp-Gly-Ser-Glu-OH     (I)

wherein X represents Glu or Gln and Y represents Trp or Arg.

The present invention relates to a monoclonal antibody capable of specifically binding to the peptide having MCF activity and antisera. The monoclonal antibody and antisera are unknown heretofore and novel.

If a substance capable of specifically reacting with the peptide having MCF activity is developed under the actual situation of the state of the art, this substance would be effectively utilized as an inhibitor of MCF activity or in the preparation of the peptide having MCF activity.

On the other hand, since MCF participates in delayed-type hypersensitivity as described above, a substance capable of specifically reacting with the peptide having MCF activity could be effectively utilized for tissue staining for surveying as to the state of participation of the immune mechanism, or in diagnosis.

From such viewpoints, it has been desired in the art to develop a substance capable of specifically reacting with the peptide having MCF activity.

SUMMARY OF THE INVENTION

The present invention has been made to meet the above requirement in the art. As a result of investigations on a substance capable of specifically reacting with the peptide having MCF activity from various aspects, attention has been brought to an antibody, especially to a monoclonal antibody as such a substance.

Thus, the present inventors have newly found that a hybridoma cell line obtained by chemically synthesizing a peptide having MCF activity, binding a carrier protein to the peptide, immunizing an animal with the protein-bound peptide used as an immunogen, and fusing lymphocytes from the animal with myeloma cells, is capable of specifically reacting with MCF to produce a monoclonal antibody sufficient for the purpose described above. The present invention has then been accomplished.

DETAILED DESCRIPTION OF PREFERRED EMBODIMENTS

Next, the present invention is described in detail.

In order to prepare the monoclonal antibody of the present invention, an antigen should firstly be prepared. In the present invention, the antigen is prepared by (1) biochemical method using a vital sample or its culture, or (2) chemical synthesis in which amino acid is chemically bound in sequence; the antigen is bound to a carrier protein such as hemocyanin of limpet, serum albumin, ovalbumin, etc., for example, using a reagent for binding peptide to protein such as glutaraldehyde, to provide for use. Specifically, the antigen is prepared by the following methods.

(1) Biochemical method using a vital sample or its culture a) Method using human peripheral blood lymphocyte For preparing the peptide (hereafter sometimes simply referred to as the peptide of the present invention) having MCF activity in the present invention, there is a method using human peripheral blood lymphocytes (hereafter simply referred to as PBL).

PBL can be obtained by isolating lymphocytes by their specific gravity, using human peripheral blood.

That is, peripheral blood overlays on Histohypaque solution manufactured by Sigma Co. or on Ficoll or Percoll solution manufactured by Pharmacia Fine Chemicals, having an appropriate specific gravity and a centrifuging force such as 1500 rpm×20 min is applied, whereby a lymphocyte-abundant fraction can be obtained. This fraction is stuck on a plastic Petri dish, although non-adherent cells may also be used as lymphocytes.

To prepare the peptide of the present invention, PBL is suspended in a medium conventionally used, for example, 10% fetal calf serum-containing RPMI 1640 medium and lectin (concanavalin A, phytohemagglutinin, etc.) is added to the suspension followed by incubation. It is preferred to use lymphocytes cultured for an appropriate time period, e.g., 20 hours, since an efficiency of the incubation is good.

In order to obtain the peptide of the present invention, PBL is resuspended in serum-free medium. After culturing in a conventional manner, for example, at 37° C. for an hour to several days in the presence of 5% $CO_2$, the resulting supernatant is used.

PBL cells may also be homogenized as they are, without performing resuspension of PBL in serum-free medium and incubation, and then centrifuged to remove relatively large cell organs. The resulting supernatant (cell lysate) may also be used. In this case, the centrifugation may be carried out, e.g., at $10,000 \times g$ for about 20 minutes.

In order to obtain the peptide of the present invention from the culture supernatant of PBL or its cell lysate, a high molecular fraction is removed from the culture supernatant or cell lysate by a method for separation such as ultrafiltration, etc., utilizing a difference in molecular size. The solution is adsorbed to an anion exchanger. By increasing the salt concentration, the peptide can be eluted. As the anionic exchanger, DEAE (diethylaminoethyl exchanger) or QAE (quaternary aminoethyl exchanger) and further Mono Q manufactured by Pharmacia Fine Chemicals may also be used.

The thus obtained active fraction may further be adsorbed onto the cationic exchanger. By increasing a salt concentration, the peptide can be eluted. As the cationic exchanger, Mono S manufactured by Pharmacia Fine Chemicals or carboxymethyl exchanger may be used.

In addition, the thus obtained active fraction may be subjected to reverse phase chromatography. By increasing an organic solvent such as acetonitrile, etc., the peptide can be eluted and obtained in a substantially pure form.

b) Method using established cells

As a raw material for preparing the novel peptide of the present invention, established cells may be used. Disregarding efficiency of the raw material, leukemia cell line CEM, etc., may also be used. However, it is preferred to use a hybridoma between peripheral blood lymphocyte and leukemia cell line, since the peptide of the present invention can be efficiently prepared.

In order to prepare the peptide of the present invention using established cells, the procedures adopted for preparation of the peptide of the present invention using PBL may be used as they are.

The peptide purified or partially purified in a) and b) above can be used as the antigen.

(2) Chemical synthesis in which amino acid is chemically bound in sequence

As the chemical synthesis method of peptide, solid phase synthesis has widely been used. This method may also be applied to synthesis of the peptide of the present invention.

In the solid phase synthesis, reactive side chains of various amino acid moieties are protected with appropriate protective groups, whereby chemical reactions that might occur on the reactive side chains can be prevented until the protective groups are finally removed. For example, as protective groups for side chains in Asp and Glu, OBzl and OtBu may be used; as protective groups for side chains in Ser, Thr and Tyr, Bzl, Br-Z and tBu may be used; further, as protective groups for side chains in Lys, Cl-Z and Tos may be used; as protective groups for side chains in Arg, Tos, MTS and Mtr may be used; as protective groups for side chains in His, Tos, DNP and Trt.OH may be used; as protective groups for side chains in Trp, CHO may be used; and as protective groups for side chains in Cys, 4-MeBzl and 4-MeOBzl may be used. Met may be protected in the form of sulfoxide. Representative examples of the solid phase synthesis are Boc method and Fmoc method. Both methods may be applied to synthesis of the peptide of the present invention. The solid phase synthesis can be initiated from the C-terminal of the peptide, using, e.g., α-amino-protected amino acid. Appropriate starting materials may be prepared by adding necessary α-amino-protected amino acids to chloromethyl resin, oxymethyl resin or benzhydrylamine resin. Furthermore, α-amino-protected and side chain-protected amino acid-added 4-(oxymethyl)-phenylacetamidemethyl resin is commercially available and this resin may also be used for synthesis of the peptide of the present invention. In addition, the peptide of the present invention may also be synthesized using an automated solid phase synthesizer.

Typical steps for peptide synthesis by the Boc method are shown below. As a starting material, for example, amino acid resin obtained by protecting the α-amino group with Boc group is used.

1. Washing with DCM (3 times)
2. Removal of Boc with TFA/DCM
3. Washing with DCM (3 times)
4. Neutralization with DIEA/DMF
5. Washing with DMF (5 times)
6. Reaction with Boc-amino acid anhydride
7. Washing with DCM (5 times)
8. Repeating steps 2 through 7
9. Washing with DCM (twice)
10. Drying with Ar gas
11. Addition of anisole/methyl sulfide
12. Addition of HF at −70° followed by reaction at −20° C. for 30 minutes and then at 0° C. for 30 minutes
13. Removal of HF by distillation
14. Washing with chloroform/ether (3 times)
15. Extraction of the synthesized peptide with 5N-acetic acid aqueous solution
16. Purification of the synthesized peptide by HPLC Typical steps for peptide synthesis by the Fmoc method are shown below. As a starting material, for example, amino acid resin obtained by protecting the α-amino group with Boc group is used.

1. Washing with DCM (3 times)
2. Removal of Boc with TFA/DCM
3. Washing with DCM (3 times)
4. Washing with DCM (3 times)
5. Reaction with Fmoc-amino acid anhydride
6. Washing with DMF (5 times)
7. Removal of Fmoc with piperidine/DMF
8. Repeating steps 4 through 7
9. Washing with DMF (5 times)
10. Washing with DCM (twice)
11. Drying with Ar gas -continued 12. Addition of anisole/methyl sulfide and then 1,2-ethanedithiol
13. Addition of HF at −70° followed by reaction at −20° C. for 30 minutes and then at 0° C. for 30 minutes
14. Removal of HF by distillation
15. Washing with chloroform/ether (3 times)
16. Extraction of the synthesized peptide with 5N-acetic acid aqueous solution
17. Purification of the synthesized peptide by HPLC Where amino acids, peptides, protective groups, activated groups, etc., are shown by abbreviations in the present specification, symbols defined in IUPAC and IUP or recognized in the art of peptide chemistry are used. Examples of the symbols are as follows.

| | |
|---|---|
| Ala | L-alanine |
| Arg | L-arginine |
| Asn | L-asparagine |
| Asp | L-aspartic acid |
| Cys | L-cystein |
| Gln | L-glutamine |
| Glu | L-glutamic acid |
| Gly | glycine |
| His | L-histidine |
| Ile | L-isoleucine |
| Leu | L-leucine |
| Lys | L-lysine |
| Met | L-methionine |
| Phe | L-phenylalanine |
| Pro | L-proline |
| Ser | L-serine |
| Thr | L-threonine |
| Trp | L-tryptophan |
| Tyr | L-tyrosine |
| Val | L-valine |
| HPLC | high performance liquid chromatography |
| ODS column | C18 column |
| HMP resin | hydroxymethylphenoxyacetic acid resin |
| PAM resin | phenylacetamide resin |
| BHA resin | benzhydrylamine resin |
| DCM | dichloromethane |
| DMF | dimethylformamide |
| TFA | trifluoroacetic acid |
| Ar gas | argon gas |
| Bzl | benzyl group |
| tBu | t-butyl group |
| Z | benzyloxycarbonyl group |
| Boc | butyloxycarbonyl group |
| Tos | tosyl group |
| MTS | mesitylene-2-sulfonyl group |
| Trt | trityl group |
| DNP | 2,4-dinitrophenyl group |
| Mtr | 4-methoxy-2,3,6-trimethylbenzenesulfonyl group |
| Fmoc | 9-fluorenylmethoxycarbonyl group |

The peptide synthesized by the chemical method described above can be used as the antigen.

Further, the antigen used in the present invention may also be prepared not only by the method described above but also by other chemical synthesis methods or genetic manipulation technique which comprise preparing DNA corresponding to the peptide, inserting DNA into a suitable vector and then expressing the same in animal cells or a microorganism.

Even though an animal may be immunized with the peptide alone, the antibody is not produced on some occasions; in such a case, carrier protein may be utilized. As the carrier protein, those conventionally used in the art may be appropriately used. For example, hemocyanin of limpet, blood serum albumin, ovalbumin, etc., may be used.

Next, the monoclonal antibody is prepared using this peptide. The preparation may be performed following the method of, e.g., Kohler and Milstein (Nature, 256, 495-497, 1975), or the method described in Japanese Patent Publication No. 58-45407 or 59-2276.

That is, an animal is immunized with the peptide, if necessary and desired, using adjuvant in combination. Sera are subjected to bioassay by, e.g., ELISA, whereby it is confirmed that the sera is capable of reacting with the peptide.

From the thus immunized animal, lymphocytes are collected. For preparation of lymphocytes, spleen, lymph nodes, peripheral blood and the like are used. The lymphocytes are fused with myeloma cells. As the myeloma cells, known strains of which specific enzyme is deficient, for example, mouse myeloma P3-X63-Ag8-Ul (P3-Ul), P3-X63-Ag8-653(X63-653), P3-NS1-1-Ag4-1(NS-1), rat myeloma 210-RCY3-Ag123, etc., are appropriately used. The cell fusion is carried out in a conventional manner, using polyethylene glycol, Sendai virus, etc. as a fusing agent.

After completion of cell fusion, a hybridoma is selected from selective medium, for example, HAT (hypoxanthine-aminoputerine-thymidine) medium.

The hybridoma which produces an antibody to the peptide is selected by enzyme-linked immunosorbent assay later described. Then by repeating cloning several times according to the limiting dilution method, the hybridoma capable of producing monoclonal antibody can be obtained.

The thus obtained monoclonal antibody-producing hybridoma cell line is intraperitoneally inoculated to a preferably syngeneic animal. After proliferating, the ascites is collected or cultured in an incubator to obtain the desired monoclonal antibody.

If necessary and desired, the thus obtained antibody can be purified and provided for use. That is, purification can be carried out using techniques conventionally applied to proteins, such as fractionation with ammonium sulfate, ion exchange, gel filtration, affinity chromatography, etc.

Next, the present invention is described with reference to examples.

EXAMPLES (1) Immunization of animal and preparation of antibody-producing cells

Mice of 8 to 10 weeks age, desirably 8 weeks age, are immunized with peptide (peptide A) having amino acid sequence (I), which has been bound to limpet hemocyanin using glutaraldehyde, (i.e., antigen B), to prepare antibody-producing cells from spleen, lymph nodes and peripheral blood of the animal. The mice to be immunized are preferably pretreated with limpet hemocyanin used as a carrier protein to render immune tolerance.

The immunization is performed as follows. Antigen B is administered to the animal subcutaneously, intravenously or intraperitoneally, together with a suitable adjuvant (for example, complete Freund's adjuvant or aluminum hydroxide gel and pertussis vaccine, etc.). Thereafter, antigen B is administered 2 to 5 times every other week to every two other weeks. On Day 3 to Day 7 after each immunization, blood is collected from the orbital plexus. It is examined by the enzyme-linked immunosorbent assay shown below (Enzyme-Linked Immunosorbent Assay (ELISA): published by Igaku Shoin Publishing Co., 1976), etc., that its serum reacts with peptide A.

Enzyme-linked immunosorbent assay

Peptide A (10 to 1000 μg/ml) is separately charged in a 96-well plate for EIA (manufactured by Flow Laboratories, Co.) by 100 to 200 μl/well. After allowing to stand at 4° C. for overnight to 2 nights, the supernatant is withdrawn. Thereafter 100 to 200 μl/well of 10% BSA (bovine serum albumin)-PBS is separately charged followed by allowing to stand at 4° C. for overnight to 2 nights. The binding residue to the protein remained on the plate is blocked (blocking). Then, BSA-PBS is discarded and 100 μl/well of a sample (mouse serum, hybridoma culture supernatant, crude monoclonal antibody) diluted with BSA-PBS is separately charged as a first antibody followed by allowing to stand at 4° C. for overnight. After washing once with resin water and 6 times with 2 M NaCl solution, 100 μl/well of 100-fold dilution of goat biotinylated anti-mouse immunoglobulin IgG (manufactured by Vector Laboratories, Co., marketed by Funakoshi Pharmaceutical Co., Ltd.) as a second antibody. The mixture is allowed to stand at room temperature for 15 minutes. After washing with PBS, 100 μl/well of 50-fold dilution of peroxidase-bound avidin-biotin complex (same as above) is separately charged followed by allowing to stand at room temperature for 15 minutes.

After further thoroughly washing with PBS, a color formed is measured at absorbance of $OD_{415\ nm}$, using ABTS substrate solution [solution obtained by adding 1 μl/ml of hydrogen peroxide to a solution of 550 mg of o diammonium 2,2'-azinobis(3-ethylbenzothiazoline-6-sulfonic acid) in 1 liter of 0.1M citrate buffer (pH 4.2), immediately before use). In this case, the mouse which strongly reacts with peptide A is used as a source for supplying antibody-producing cells for the preparation of hybridoma.

Where the cells per se are used as antigen in the enzyme-linked immunosorbent assay, target cells are cultured in Falcon 3072 plate and 0.25% glutaraldehyde-PBS is added to the plate. After allowing to stand at room temperature for 1 to 2 hours, the mixture is thoroughly washed with PBS. Then 100 to 200 μl of 1% BSA-PBS is added and the resulting mixture is allowed to stand for 2 hours. After thoroughly washing with resin water or PBS, an antibody titer is determined by the method using a conventional antigen-coated plate, using the plate.

In providing for the cell fusion, antigen B is intraperitoneally administered to the immunized mice in a dose of 20 to 400 μg/mouse, 3 to 4 days before the fusion treatment. The spleen is withdrawn to prepare spleen cells. That is, the spleen is minced in MEM (manufactured by Nissui Pharmaceutical Co., Ltd.) and loosened with tweezers. After centrifugation at 1200 rpm for 5 minutes, the supernatant is discarded and the residue is treated with Tris-ammonium chloride buffer (pH 7.65) for 1 to 2 minutes to remove erythrocytes. After washing 3 times with MEM, the cells are provided as spleen cells for fusion.

(2) Preparation of myeloma cells

As myeloma cells, established cells obtained from mice are used. Examples of the myeloma cells used include 8-azaguanine-resistant mouse (derived from BALB/c) myeloma cell line P3-X63Ag8-Ul(P3-Ul) (Current Topics in Microbiology and Immunology-1) (European J. Immunology, 6, 511–519 (1976)), SP2/0-Ag14(SP-2) (Nature, 276, 269–270 (1978)), P3-X63-Ag8653 (653) (J. Immunology, 123, 1548–1550 (1979)), P3-X63-Ag8 (X63) (Nature, 256, 495–497 (1975)), NS-1 (formal name: P3/NSl/1-Ag4-1) (European J. Immunology, 6, 511 (1976)) (purchased from Dainippon Pharmaceutical Co., Ltd.), etc.

These cell lines are subcultured in 8-azaguanine medium (normal medium obtained by supplementing glutamine (1.5 mM), 2-mercaptoethanol ($5 \times 10^{-5}$ M), gentamycin (10 μg/ml) and fetal calf serum (FCS) (manufactured by Hiclone Laboratories, Inc.) (10%) to normal medium, to which 8-azaguanine (15 μg/ml) is further added) but, the cell lines are cultured in normal medium 3 to 4 days before the cell fusion, thereby to ensure cell counts of $2 \times 10^7$ or more on the day when the fusion is performed.

In this example, NS-1 is used among the cells lines described above.

(3) Cell fusion

The antibody-producing cells immunized in (1) and the myeloma cells obtained in (2) are thoroughly washed with MEM medium or PBS and mixed with each other so as to have cell counts of the antibody-producing cells to the myeloma cells=5 to 10:1. After centrifugation (1,200 rpm, 5 minutes), the supernatant is discarded and the precipitated cells are fully loosened. While stirring, 0.2 to 1 ml/$10^3$ antibody-producing cells are added to a mixture of 2 g of polyethylene glycol 1,000 (PEG-1,000), 2 ml of MEM and 0.7 ml of dimethylsulfoxide at 37° C. After adding 1 to 2 ml of MEM to the mixture several times every one or two other minutes, MEM is added to make the whole volume 50 ml. After centrifugation (900 rpm, 5 minutes), the supernatant is discarded and the cells are gently loosened. Then 100 ml of normal medium (RPMI-1640, FCS 10%) is added to the cells. The cells are slowly suspended by suction and blowing with a cylinder pipette.

The suspension is separately charged by 1 ml/well each on a 24-well culture plate and cultured at 37° C. for 24 hours in a 5% $CO_2$ incubator. To the culture plate is added 1 ml/well of HAT medium (medium obtained by supplementing hypoxanthine ($10^{-4}$M), thymidine ($1.5 \times 10^{-5}$M) and aminoputerine ($4 \times 10^{-7}$M) to normal medium). Incubation is continued for further 24 hours. Thereafter, incubation is carried out at 37° C. for 10 to 14 days in a 5% $CO_2$ incubator, while discarding 1 ml of the culture supernatant and freshly supplementing the same volume of HAT medium, every 24 hours for 2 days.

With respect to the well in which the fused cells grown to make colonies are recognized, 1 ml of the supernatant is discarded and the same volume of HT medium (medium obtained by removing aminoputerine from HAT medium) is supplemented. For subsequent 2 days, substitution with HT medium is performed every 24 hours.

After culturing in HT medium for 3 to 4 days, a part of the culture supernatant is taken out and an antibody titer to peptide A is determined by the enzyme-linked immunosorbent assay. Cloning is repeated twice by the limiting dilution method. The fused cell in which a potent antibody titer is stably noted to peptide A is selected as anti-MCF-monoclonal antibody-producing hybridoma.

(4) Preparation of monoclonal antibody

The anti-MCF-monoclonal antibody-producing hybridoma obtained in (3) is intraperitoneally injected to C57BL/6 strain female mice of to 10 weeks age, which have been subjected to Pristane treatment (intraperitoneally administering 0.5 ml of 2,6,10,14-tetramethylpentadecane (Pristane) and then feeding for 2 weeks) in a dose of 2 to $4 \times 10^6$/mouse. The hybridoma is changed to ascites tumor in 10 to 21 days. From the mouse, the ascites is collected and centrifuged (3,000 rpm, 5 minutes) to remove the solid. Salting out with 50% ammonium sulfate is carried out followed by dialysis with a solution obtained by adding 0.5 M NaCl to PBS. The dialysate is passed through a column of Sephacryl S300 (manufactured by Pharmacia Fine Chemicals, Inc.) (bed volume, 750 ml) at a flow rate of 15 ml/hr. IgG and IgM fractions are collected and made purified monoclonal antibody.

Isotype of the antibody is determined by the Ouchterlony method (double immunodiffusion) (Guideline to Immunological Experiment, Biochemical Experiment 15, published by Gakkai Shuppan Publishing Co., page 74, 1981).

The protein is quantitatively determined by the Folin method and calculated from absorbancy at 280 nm (1.4 ($OD_{280}$) ≈ 1 mg/ml of immunoglobulin).

Binding ability of the thus obtained monoclonal antibody to peptide A and subtype of immunoglobulin are shown in Table 1.

TABLE 1

| Monoclonal Antibody | | Binding Ability to Antigen (synthetic peptide) ELISA $OD_{415\ nm}$ | | |
| --- | --- | --- | --- | --- |
| Clone No. | Subclass | Peptide A | Peptide N | Peptide C |
| 96 | IgM | 0.55 | 0.94 | 0.33 |
| 111 | IgM | 1.04 | 0.81 | 0.39 |
| 113 | IgM | 0.65 | 0.27 | 0.51 |
| 119 | IgM | 1.12 | 0.74 | 0.72 |
| 122 | IgM | 1.02 | 0.89 | 0.66 |
| 126 | IgM | 0.99 | 0.68 | 0.50 |
| 127 | IgM | 0.95 | 0.54 | 0.55 |
| 128 | IgM | 0.89 | 0.77 | 0.62 |

TABLE 1-continued

| Monoclonal Antibody | | Binding Ability to Antigen (synthetic peptide) ELISA $OD_{415\ nm}$ | | |
| --- | --- | --- | --- | --- |
| Clone No. | Subclass | Peptide A | Peptide N | Peptide C |
| 129 | IgM | 0.76 | 0.86 | 0.37 |
| 130 | IgM | 0.98 | 0.70 | 0.89 |
| 133 | IgM | 1.06 | 1.10 | 1.06 |
| 141 | IgM | 0.91 | 0.72 | 0.68 |
| 156 | IgM | 0.96 | 0.83 | 0.93 |
| 173 | IgM | 0.96 | 0.87 | 0.81 |
| 175 | IgM | 0.93 | 0.92 | 0.87 |
| 184 | IgM | 0.80 | 0.68 | 1.00 |
| 189 | IgM | 0.87 | 0.65 | 0.83 |
| 195 | IgM | 0.91 | 0.87 | 0.93 |
| 201 | IgG | 0.88 | 0.76 | 0.83 |
| 204 | IgG | 0.92 | 0.45 | 0.50 |
| Negative control | — | 0.09 | 0.29 | 0.20 |

In the table, peptide A, peptide N and peptide C represent Trp-Leu-Gly-Arg-Glu-Asp-Gly-Ser-Glu, Trp-Leu-Gly-Arg-Glu and Glu-Asp-Gly-Ser-Glu, respectively.

The monoclonal antibody in accordance with the present invention is a novel substance which is unknown heretofore. The monoclonal antibody has a property of being capable of specifically reacting with lymphokine or cytokine having macrophage chemotactic activity. Therefore, the present invention can be effectively utilized particularly for the clarification of various immune mechanisms or tissue staining, or in the medical and biochemical fields such as diagnosis, etc., in addition to isolation and purification of MCF.

While the invention has been described in detail and with reference to specific embodiments thereof, it is apparent to one skilled in the art that various changes and modifications can be made therein without departing from the spirit and the scope of the present invention.

What is claimed is:

1. A monoclonal antibody which specifically binds to a peptide represented by amino acid sequence I below:

H-Y-Leu-Gly-Arg-X-Asp-Gly-Ser-Glu-OH    I wherein X represents Glu or Gln and Y represents Trp or Arg.

* * * * *